United States Patent
Kratzmeier et al.

(10) Patent No.: US 9,297,807 B2
(45) Date of Patent: Mar. 29, 2016

(54) PROTEIN ANALYSIS USING A POLYMETHINE MARKER DYE

(75) Inventors: Martin Kratzmeier, Waldbronn (DE); Xiaodan Tian, Karlsruhe (DE); Fritz Bek, Pfinztal (DE)

(73) Assignee: Agilent Technologies, Inc., Santa Clara, CA (US)

( * ) Notice: Subject to any disclaimer, the term of this patent is extended or adjusted under 35 U.S.C. 154(b) by 1423 days.

(21) Appl. No.: 12/279,046

(22) PCT Filed: Feb. 10, 2006

(86) PCT No.: PCT/EP2006/050862
§ 371 (c)(1),
(2), (4) Date: Jan. 8, 2009

(87) PCT Pub. No.: WO2007/090468
PCT Pub. Date: Aug. 16, 2007

(65) Prior Publication Data
US 2009/0200167 A1    Aug. 13, 2009

(51) Int. Cl.
*G01N 33/68* (2006.01)
*G01N 33/92* (2006.01)
*C09B 23/06* (2006.01)

(52) U.S. Cl.
CPC ............ *G01N 33/6839* (2013.01); *C09B 23/06* (2013.01); *G01N 33/92* (2013.01)

(58) Field of Classification Search
CPC ....... B01D 57/02; G01N 33/68; G01N 33/92; C09B 23/06
USPC .......... 204/403.01–403.15; 205/777.5–794.5; 600/345–348; 435/4–40.52; 422/68.1–98; 436/62–71, 500–548
See application file for complete search history.

(56) References Cited

U.S. PATENT DOCUMENTS

| | | | |
|---|---|---|---|
| 6,750,346 B2 * | 6/2004 | Czerney et al. | 546/66 |
| 2002/0115862 A1 | 8/2002 | Czerney et al. | |
| 2003/0015429 A1 * | 1/2003 | Dubrow et al. | 204/603 |
| 2004/0162423 A1 | 8/2004 | Czerney et al. | |
| 2005/0027111 A1 * | 2/2005 | Chow et al. | 530/412 |

FOREIGN PATENT DOCUMENTS

| | | |
|---|---|---|
| EP | 1391723 | 2/2004 |
| JP | 06-123740 A | 5/1994 |
| JP | 11-326277 A | 11/1999 |
| JP | 2003-534435 A | 11/2003 |
| JP | 2005-099031 A | 4/2005 |
| JP | 2005-526956 A | 9/2005 |

OTHER PUBLICATIONS

Notification of Reason for Rejection (Office Action) for Japanese Application No. 2008-553,635 mailed on Aug. 9, 2011 (4pages).
Weiller,Bruce H. et al., "Analysis of Lipoproteins by Capillary Zone Electrophoresis in Microfluidic Devices: Assay Development and Surface Roughness Measurements", Anal. Chem., Apr. 1, 2002, pp. 1702-1711, vol. 74, No. 7.
Ceriotti, Laura et al., "Low-density lipoprotein analysis in microchip capillary electrophoresis systems", Electrophoresis, Oct. 2002, pp. 3615-3622, vol. 23, No. 20.
Kim, Joo-Eun, "Functional Membrane-Implanted Lab-on-a-Chip for Analysis of Percent HDL Cholesterol", Anal. Chem., Dec. 15, 2005, pp. 7901-7907, vol. 77, No. 24.
Schmidt, Gerd et al., "Analytical capillary Isotachophoresis of human serum lipoproteins". Electrophoresis, Sep. 1997, pp. 1807-1813, vol. 18, No. 10.
Dyomics Catalogue, "Fluorescent Dyes for Bioanalytical and Hightech Applications", 4th Ed.—autumn 2005, Dyomics GBMH, Jena, Germany, XP002385175, URL: 222.dyomics.com.
EPO Examination Report dated Jan. 27, 2009, EP Application No. 06 708 204.0, 4 pages.

* cited by examiner

*Primary Examiner* — Susan D Leong

(57) ABSTRACT

A kit for optically detecting proteins, in particular lipoproteins, in a sample, the kit comprising: a chip for performing a separation of the proteins, in particular of the lipoproteins, wherein the chip comprises at least one well for receiving the sample, and a separation channel coupled to the at least one well and being adapted for separating different compounds and a marker dye which contains a polymethine of the general formula (I) wherein Z is a substituted derivative of benzooxazole, benzodiazole, 2,3,3-trimethylindolinine, 2,3,3-trimethyl-4,5-benzo-3H-indolinine, 3- and 4-picoline, lipidine, chinadine and 9-methylacridine derivatives with the general formula IIa or IIb or IIc and wherein X is selected from the group consisting of O, S, Si, N-alkyl and C(alkyl)$_2$, n is 0, 1, 2 or 3, $R^1$ to $R^{14}$ are independently selected from the group consisting of hydrogen, alkyl, alkoxy, cycloalkyl, linear or branched alkenyl, cycloalkenyl, aryl, heteroaryl, heterocycle, hydroxy, carboxy, amine, alkyl-substituted amine and cyclic amine and/or two or more fragments in ortho-position to each other, for example $R^{10}$ and $R^{11}$ or $R^4$, $R^5$ and $R^6$, together form another cycloalkyl ring or ring system, heterocyclic ring or ring system, heteroaryl ring system or aromatic ring or ring system.

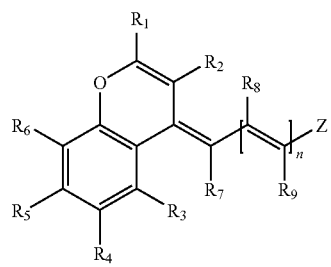

I

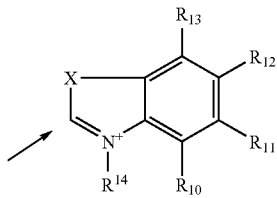

IIa

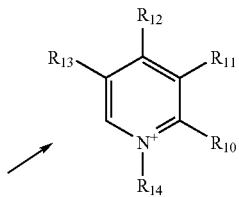

IIb

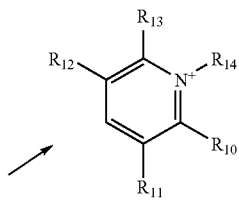

IIc

16 Claims, 8 Drawing Sheets

PROTEIN ANALYSIS USING A POLYMETHINE MARKER DYE

BACKGROUND ART

The present invention relates to a kit for optically detecting proteins, to a method for optically detecting proteins, to a method of analysing proteins and to the use of polymethines for optically detecting proteins in a sample.

Determination of the circulating levels of plasma lipoproteins is important in the diagnosis of primary and secondary disorders of lipid transport and in risk assessment for arteriosclerosis and coronary artery disease. In the fasting state, three main lipoprotein classes have been identified: VLDL (very low density lipoproteins), LDL (low density lipoproteins) and HDL (high density lipoproteins), each of which differs in size and density, and in lipid and apolipoprotein composition.

It is well established that there is a positive correlation between risk of premature coronary heart disease and total plasma cholesterol and plasma LDL-cholesterol (LDL-C). There is also a correlation between decreased HDL-cholesterol (HDL-C) and increased plasma TG (triglycerides). Heterogeneity in the size and density of LDL is well documented and has also been shown to have clinical relevance. Small dense LDL (Pattern B) has an increased relative risk compared with large light LDL (Pattern A). One of the most prevalent lipid/lipoprotein patterns associated with risk of coronary artery disease is the atherogenic lipoprotein phenotype (ALP), which is characterized by moderately raised plasma TG, low levels of HDL-C, elevated total and LDL-C, and small, dense LDL particles. Although methods are available in the clinical laboratory for measurement of HDL, LDL and VLDL, methods for the identification of the predominant LDL subclass are technically difficult and time-consuming.

The main methods for separation and analysis of the plasma lipoprotein levels, based on differences in physical properties, include ultracentrifugation, electrophoresis and differential precipitation. Of these, ultracentrifugation is seen in the prior art as the "gold standard" for analysis of plasma lipoproteins and potentially provides the greatest amount of information, as the lipid and apolipoprotein compositions of the separated lipoproteins can be analysed.

Methods for density gradient centrifugation have generally been based on salt solutions, and include sequential flotation with adjustment of the density of the plasma and infranatants after each centrifugation step, or centrifugation on discontinuous or continuous gradients. The use of salt gradients has a number of disadvantages. These are technically difficult to prepare and relatively unstable, and reproducibility is difficult to achieve. In addition, prolonged centrifugation is often necessary to float the lipoproteins into the gradients and the high salt concentrations can modify the protein structure and lead to loss of apolipoproteins from the lipoprotein fractions. For further analysis of the lipoprotein fractions, it is usually necessary to remove the salt, e.g., by dialysis. This results in loss of material and poor recoveries.

Hence, it would be desirable to provide improved methods for analysing lipoproteins and in particular for characterizing sub-class patterns of the lipoproteins in order to better characterize the atherogenic risk of a patient and to obtain more information for managing patients.

DISCLOSURE

It is an object of the invention to provide improved kits and methods for detecting and analysing proteins, in particular lipoproteins. The object is solved by the independent claims. Preferred embodiments are shown by the dependent claims.

According to one embodiment of the present invention, a kit for optically detecting proteins, in particular lipoproteins, in a sample is provided. The kit comprises a chip for performing a separation of the proteins, in particular of the lipoproteins, wherein the chip comprises at least one well for receiving the sample and a separation channel coupled to the at least one well and being adapted for separating different compounds. According to this embodiment, the kit further comprises a marker dye which contains a non-symmetrical polymethine comprising a substituted ω-(benz[b]pyran-4-ylidene)alk-1-enyl) unit of the general formula I

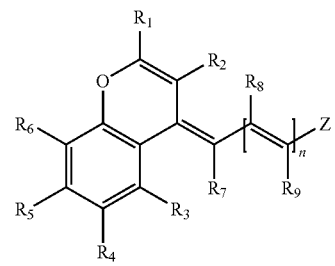

wherein Z is a substituted derivative of benzooxazole, benzodiazole, 2,3,3-trimethylindolinine, 2,3,3-trimethyl-4,5-benzo-3H-indolinine, 3- and 4-picoline, lipidine, chinadine and 9-methylacridine derivatives with the general formula IIa or IIb or IIc

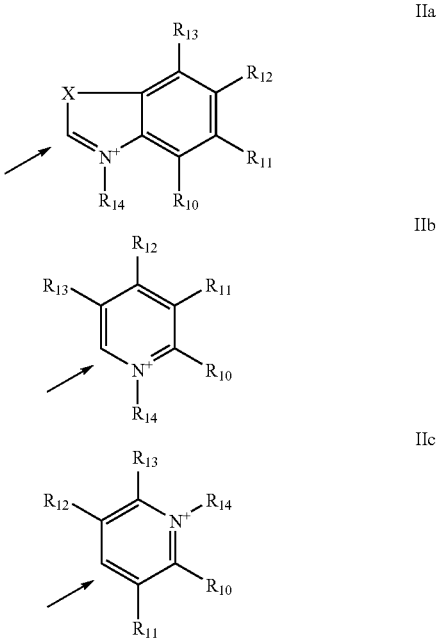

and wherein

X is selected from the group consisting of O, S, Si, N-alkyl and C(alkyl)$_2$, n is 0, 1, 2 or 3, $R^1$ to $R^{14}$ are independently selected from the group consisting of hydrogen, alkyl, alkoxy, cycloalkyl, linear or branched alkenyl, cycloalkenyl, aryl, heteroaryl, heterocycle, hydroxy, carboxyl, amine, alkyl-substituted amine and cyclic amine and/or two or more fragments in ortho-position to each other, for example $R^{10}$ and $R^{11}$ or $R^4$, $R^5$ and $R^6$, together form another cycloalkyl ring or ring system, heterocyclic ring or ring system, heteroaryl ring system or aromatic ring or ring system.

In particular, the kit is advantageous for the analysis of lipoproteins, in that the marker dye as defined above has a high affinity for the hydrophobic inner compartment of lipoprotein particles, with little or no staining activity for other types of proteins or nucleic acids. By mixing, e.g. human serum samples with this dye and subsequent electrophoretic analysis in a microfluidic chip, the high density lipoprotein (HDL) sub-fraction of lipoproteins can be baseline separated from the low density lipoprotein (LDL) sub-fraction. Moreover, the HDL sub-fraction can be resolved into at least four to five individual sub-populations that can be quantitatively analysed. This kit enables rapid and reproducible analysis for, e.g. patient serum samples for lipoprotein class distribution, i.e. percentage of HDL versus LDL, and also for HDL and LDL sub-patterns.

According to a further embodiment of the present invention, a method of analysing proteins, in particular lipoproteins, in a sample is provided. The method comprises a step in which the proteins, in particular the lipoproteins, are separated in at least one dimension. The method further comprises a step in which the proteins, in particular the lipoproteins, are labelled with a marker dye containing a polymethine of the general formula I as defined above. The method further comprises a step of optically detecting the separated and labelled proteins, in particular the labelled lipoproteins.

Embodiments of the present invention further relate to a method for optically detecting lipoproteins in a sample, wherein the method comprises a step of labelling lipoproteins with a marker dye containing a polymethine of the general formula (I) as defined above.

Finally, embodiments of the present invention relate to the use of a polymethine of the general formula I as defined above for optically detecting lipoproteins and/or for the analysis of lipoprotein class distribution and/or for the analysis of HDL and/or LDL subclass patterns in a sample by labelling the proteins with the polymethine of the general formula I.

Embodiments of the invention can be partly or entirely embodied or supported by one or more suitable software programs, which can be stored on or otherwise provided by any kind of data carrier and which might be executed in or by any suitable data processing unit. Software programs or routines can be preferably applied to the method of analysing proteins, e.g. in the step of detecting the labelled lipoproteins or in a step of calibrating the obtained signals or converting them into a gel-like image. For example, calibration steps according to an embodiment of the invention can be realized by a computer program, i.e. by software, or by using one or more special electronic optimisation circuits, i.e. in hardware, or in hybrid form, i.e. by means of software components and hardware components.

Further exemplary embodiments of the kit will be described below. However, these embodiments also apply for the method of analysing lipoproteins, for the method of optically detecting lipoproteins and for the use of polymethines of the general formula I for optically detecting lipoproteins and/or for the analysis of lipoprotein class distribution and/or for the analysis of HDL and/or LDL subclass patterns.

According to a preferred embodiment of the kit, the separation channel is adapted for separating different compounds electrophoretically, chromatographically or electrochromatographically.

According to a further preferred embodiment of the kit, the separation channel is adapted for separating different compounds electrophoretically by electrophoresis selected from the group consisting of SDS polyacrylamide electrophoresis (SDS-PAGE), capillary electrophoresis and micro-channel/microfluidic channel electrophoresis.

According to a further preferred embodiment of the kit, the chip further comprises an element for applying an electrical field across the separation channel.

According to a further preferred embodiment of the kit, the chip comprises a material selected from the group consisting of glass, quartz, silica, silicon, and polymers.

According to a further preferred embodiment, the kit further comprises a separation gel.

According to a further preferred embodiment of the kit, the separation gel is selected from the group consisting of polyacrylamide, polydimethylacrylamide, polyethylene oxide, and polyvinyl pyrrolidone and is preferably polydimethylacrylamide.

According to a further preferred embodiment, the kit further comprises a calibration sample.

According to a further preferred embodiment of the kit, the calibration sample is a "ladder".

At least one of the substituents $R^1$ to $R^{14}$ can also be a solubilising or ionisable or ionised substituent like cyclodextrine, sugar, $SO_3^-$, $PO_3^{2-}$, $COO^-$, or $NR_3^+$ which determines the hydrophilic properties of these dyes. Such a substituent may be bound to the marker dye by means of a spacer group. For example, said solubilizing or ionisable group is bound via an aliphatic or heteroaliphatic group.

Further, it is preferred that at least one of the substituents $R^1$ to $R^{14}$ is a reactive group which is capable of reacting with a protein or lipoprotein to form a covalent or non-covalent bond. Such a substituent can also be bound to the dye by means of a spacer group. Examples for such reactive groups are selected from the group consisting of an N-hydroxysuccinimidester group, a maleimide group and a phosphoamidite group.

According to a further preferred embodiment, $R^1$ to $R^{14}$ are independently selected form the group consisting of hydrogen, chlorine, bromine, and an aliphatic or mononuclear aromatic group, each having at most 12 carbon atoms which may contain as a substituted group in addition to carbon and hydrogen up to 4 oxygen atoms and 0, 1 or 2 nitrogen atoms or a sulfur atom or a sulfur and a nitrogen atom or represent an amino function, having a nitrogen atom to which there is bound hydrogen or at least one substituent having up to 8 carbon atoms, said substituent being selected from the group consisting of carbon, hydrogen and up to two sulfonic acid groups.

According to a further preferred embodiment, any of the groups $R^1$ to $R^{14}$ is aliphatic and contains from 1 to 6 carbon atoms.

Further, it is preferred that $R^1$ is a substituent which has a quaternary C-atom in α-position relative to the pyran ring. Examples for such substituents are t-butyl ($-C(CH_3)_3$), phenyl and adamantyl ($-C_{10}H_{15}$/tricyclo[$3.3.1.1^{3,7}$]decyl). It is particularly preferred that $R^1=-(CH_3)_3$.

According to a further preferred embodiment, $R^2R^3$, $R^4$, $R^6$, $R^7$, $R^8$, $R^9$, $R^{10}$, $R^{11}$, $R^{12}$ and/or $R^{13}$ is hydrogen.

According to a further preferred embodiment, $R^5$ is an amine or alkyl-substituted amine. It is particularly preferred that $R^5=-N(CH_2CH_3)_2$.

According to an alternative embodiment, $R^4$ and $R^5$ form a saturated, partially saturated or unsaturated, substituted or un-substituted heterocyclic ring, preferably a six-membered heterocyclic ring containing one or more heteroatoms, preferably one or more nitrogen atoms, more preferably one nitrogen atom. Most preferably, the nitrogen atom of the heterocyclic ring corresponds to $R^5$ and/or is substituted, e.g., by an ethyl group. It is further preferred that the heterocyclic ring contains one double bond.

According to a further alternative embodiment, $R^4$, $R^5$ and $R^6$ form a saturated, partially saturated or unsaturated, substituted or un-substituted bicyclic ring system, preferably a ten-membered bicyclic ring containing one or more heteroatoms, preferably one or more nitrogen atoms, more preferably one nitrogen atom. Most preferably, the nitrogen atom of the heterocyclic ring corresponds to $R^5$. It is further preferred that the bicyclic ring system is saturated and/or unsubstituted.

According to a further preferred embodiment, $R^{14}$ is a hydroxyl- and/or carboxyl-substituted or unsubstituted alkyl. Examples for such substituents are —$(CH_2)_3$—OH, —$(CH_2)_5$—COOH, and —$CH_3$.

According to a further preferred embodiment, X is a carbon atom. The carbon atom is preferably substituted, e.g. by one or two alkyl groups such as methyl or ethyl. Most preferably, X is —$C(CH_3)_2$.

According a further preferred embodiment, Z has the general formula IIa.

According a further preferred embodiment, n is 1.

According to a further preferred embodiment, $R^1$ is —$C(CH_3)_3$, $R^2$ is hydrogen, $R^3$ is hydrogen, $R^4$ is hydrogen, $R^5$ is —$N(CH_2CH_3)_2$, $R^6$ is hydrogen, $R^7$ is hydrogen, $R^8$ is hydrogen, $R^9$ is hydrogen, $R^{10}$ is hydrogen, $R^{11}$ is hydrogen, $R^{12}$ is hydrogen, $R^{13}$ is hydrogen, $R^{14}$ is —$(CH_2)_3$—OH, Z has the general formula IIa, X is —$C(CH_3)_2$ and/or n is 1.

According to a further preferred embodiment, $R^1$ is —$C(CH_3)_3$, $R^2$ is hydrogen, $R^3$ is hydrogen, $R^4$ is hydrogen, $R^5$ is —$NH_2$, $R^6$ is hydrogen, $R^7$ is hydrogen, $R^8$ is hydrogen, $R^9$ is hydrogen, $R^{10}$ is hydrogen, $R^{11}$ is hydrogen, $R^{12}$ is hydrogen, $R^{13}$ is hydrogen, $R^{14}$ is —$(CH_2)_3$—OH, Z has the general formula IIa, X is —$C(CH_3)_2$ and/or n is 1.

According to a further preferred embodiment, $R^1$ is —$C(CH_3)_3$, $R^2$ is hydrogen, $R^3$ is hydrogen, $R^4$ is hydrogen, $R^5$ is —$N(CH_2CH_3)_2$, $R^6$ is hydrogen, $R^7$ is hydrogen, $R^8$ is hydrogen, $R^9$ is hydrogen, $R^{10}$ is hydrogen, $R^{11}$ is hydrogen, $R^{12}$ is hydrogen, $R^{13}$ is hydrogen, $R^{14}$ is —$CH_3$, Z has the general formula IIa, X is —$C(CH_3)_2$ and/or n is 1.

According to a further preferred embodiment, $R^1$ is —$C_6H_5$, $R^2$ is hydrogen, $R^3$ is hydrogen, $R^4$ is hydrogen, $R^5$ is —$N(CH_2CH_3)_2$, $R^6$ is hydrogen, $R^7$ is hydrogen, $R^8$ is hydrogen, $R^9$ is hydrogen, $R^{10}$ is hydrogen, $R^{11}$ is hydrogen, $R^{12}$ is hydrogen, $R^{13}$ is hydrogen, $R^{14}$ is —$(CH_2)_3$—OH, Z has the general formula IIa, X is —$C(CH_3)_2$ and/or n is 1.

According to further preferred embodiments, the polymethine of the general formula I is selected from one of the following compounds III to IX. Preferred counter-ions to the compounds having the general formula I and especially to compounds III to IX are $F^-$, $Cl^-$, $Br^-$, $I^-$, $ClO_4^-$ or $BF_4^-$.

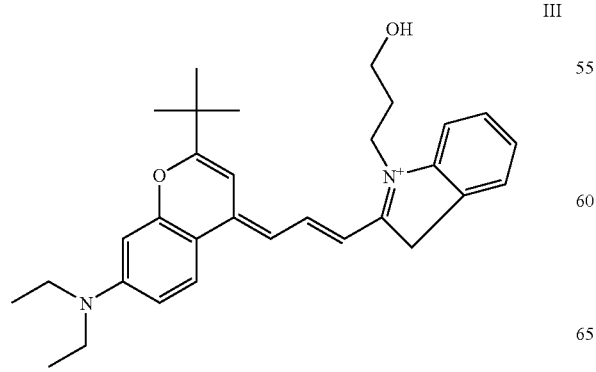

III

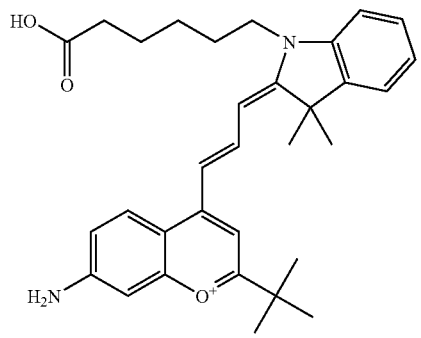

IV

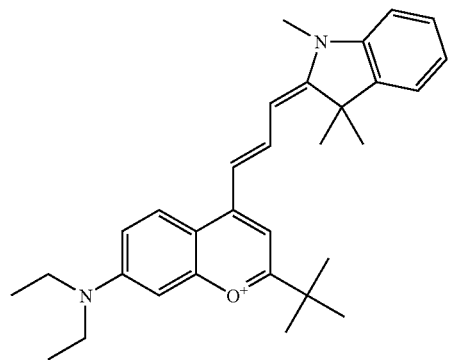

V

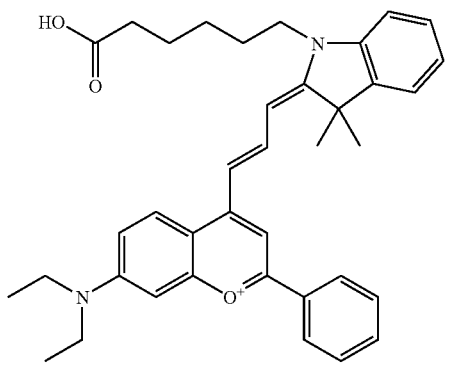

VI

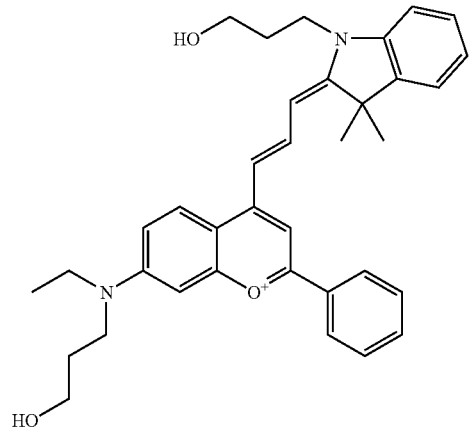

VII

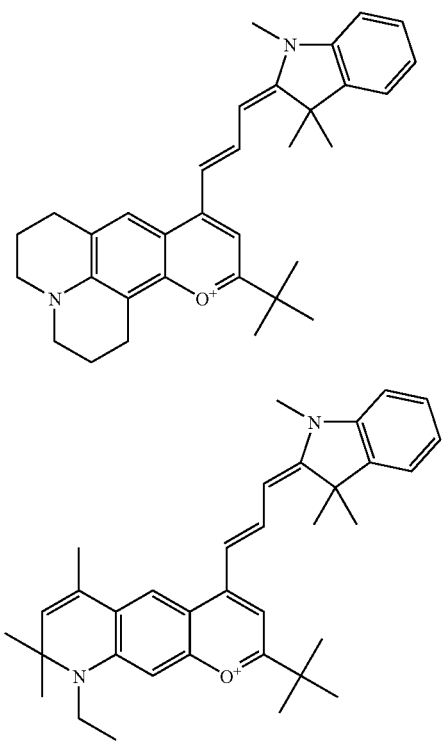

As used herein, the term "alkyl" means a linear or branched saturated aliphatic hydrocarbon group having a single radical and 1-10 carbon atoms. Examples of alkyl groups include methyl, propyl, isopropyl, butyl, n-butyl, isobutyl, sec-butyl, tert-butyl and pentyl. A branched alkyl means that one or more alkyl groups such as methyl, ethyl or propyl, replace one or both hydrogens in a —$CH_2$ group of a linear alkyl chain. The term "lower alkyl" means an alkyl of 1-3 carbon atoms.

The term "alkoxy" means an "alkyl" as defined above connected to an oxygen radical.

The term "cycloalkyl" means a non-aromatic mono- or multicyclic hydrocarbon ring system having a single radical and 3-12 carbon atoms. Exemplary monocyclic cycloalkyl rings includes cyclopropyl, cyclopentyl and cyclohexyl. Exemplary multicyclic cycloalkyl rings include adamantyl and norbornyl.

The term "alkenyl" means a linear or branched aliphatic hydrocarbon group containing a carbon-carbon double bond having a single radical and 2-10 carbon atoms.

A "branched" alkenyl means that one or more alkyl groups such as methyl, ethyl or propyl replace one or both hydrogens in a —$CH_2$ or —CH= linear alkenyl chain. Exemplary alkenyl groups include ethenyl, 1- and 2-propenyl, 1-, 2- and 3-butenyl, 3-methylbut-2-enyl, 2-propenyl, heptenyl, octenyl and decenyl.

The term "cycloalkenyl" means a non-aromatic monocyclic or multicyclic hydrocarbon ring system containing a carbon-carbon double bond having a single radical and 3 to 12 carbon atoms. Exemplary monocyclic cycloalkenyl rings include cyclopropenyl, cyclopentenyl, cyclohexenyl or cycloheptenyl. An exemplary multicyclic cycloalkenyl ring is norbornenyl.

The term "aryl" means a carbocyclic aromatic ring system containing one, two or three rings which may be attached together in a pendent manner or fused, and containing a single radical. Exemplary aryl groups include phenyl, naphthyl and acenaphthyl.

The term "heterocyclic" or "heterocycle" means cyclic compounds having one or more heteroatoms (atoms other than carbon) in the ring, and having a single radical. The ring may be saturated, partially saturated or unsaturated, and the heteroatoms may be selected from the group consisting of nitrogen, sulfur and oxygen. Examples of saturated heterocyclic radicals include saturated 3 to 6-membered hetero-monocyclic groups containing 1 to 4 nitrogen atoms, such as pyrrolidinyl, imidazolidinyl, piperidino, piperazinyl; saturated 3- to 6-membered hetero-monocyclic groups containing 1 to 2 oxygen atoms and 1 to 3 nitrogen atoms such as morpholinyl; saturated 3- to 6-membered hetero-monocyclic groups containing 1 to 2 sulfur atoms and 1 to 3 nitrogen atoms, such as thiazolidinyl. Examples of partially saturated heterocyclic radicals include dihydrothiophene, dihydropyran and dihydrofuran. Other heterocyclic groups can be 7 to 10 carbon rings substituted with heteroatoms such as oxocanyl and thiocanyl. When the heteroatom is sulfur, the sulfur can be a sulfur dioxide such as thiocanyldioxide.

The term "heteroaryl" means unsaturated heterocyclic radicals, wherein "heterocyclic" is as previously described. Exemplary heteroaryl groups include unsaturated 3 to 6-membered hetero-monocyclic groups containing 1 to 4 nitrogen atoms, such as pyrrolyl, pyridyl, pyrimidyl and pyrazinyl; unsaturated condensed heterocyclic groups containing 1 to 5 nitrogen atoms, such as indolyl, quinolyl and isoquinolyl; unsaturated 3 to 6-membered hetero-monocyclic groups containing an oxygen atom, such as furyl; unsaturated 3 to 6-membered hetero-monocyclic groups containing a sulfur atom, such as thienyl; unsaturated 3 to 6-membered hetero-monocyclic groups containing 1 to 2 oxygen atoms and 1 to 3 nitrogen atoms, such as oxyzolyl; unsaturated condensed heterocyclic groups containing 1 to 2 oxygen atoms and 1 to 3 nitrogen atoms, such as benzoxazolyl; unsaturated 3 to 6-membered hetero-monocyclic group containing 1 to 2 sulfur atoms and 1 to 3 nitrogen atoms, such as thiazolyl; and unsaturated condensed heterocyclic group containing 1 to 2 sulfur atoms and 1 to 3 nitrogen atoms, such as benzothiazolyl. The term "heteroaryl" also includes unsaturated heterocyclic radicals, wherein "heterocyclic" is as previously described, in which the heterocyclic group is fused with an aryl group, in which aryl is as previously described. Exemplary fused radicals include benzofuran, benzdioxole and benzothiophene.

As used herein, the term "heterocyclic $C_{1-4}$ alkyl", "heteroaromatic $C_{1-4}$ alkyl" and the like refer to the ring structure bonded to a $C_{1-4}$ alkyl radical, As used herein, the term "ring" or "ring system" includes cycloalkyl, cycloalkenyl, aryl, heteroaryl or heterocycle.

All of the cyclic ring structures disclosed herein can be attached at any point where such connection is possible, as recognized by one skilled in the art.

As used herein, the term "halogen" includes fluoride, bromide, chloride, or iodide.

BRIEF DESCRIPTION OF DRAWINGS

Other objects and many of the attendant advantages of embodiments of the present invention will be readily appreciated and become better understood by reference to the following more detailed description of embodiments in connection with the accompanied drawings.

Figure 1:
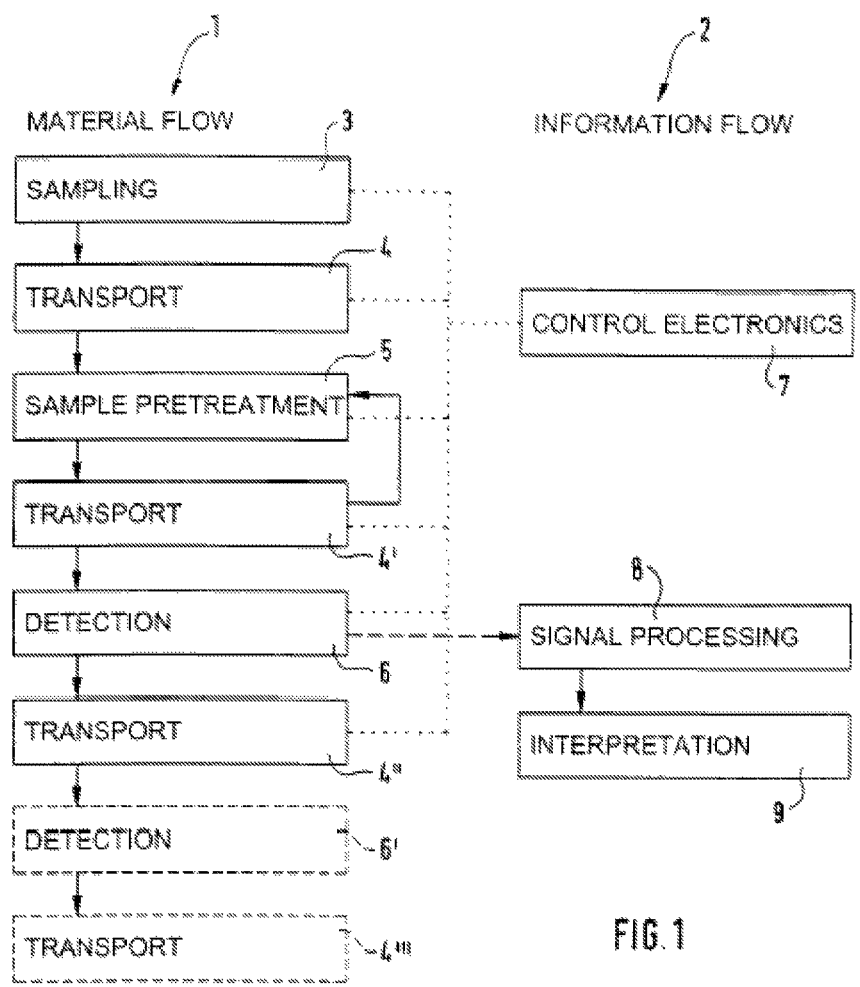
FIG. 1 schematically illustrates the functional components required for a chip for utilization in the kit according to the present invention, illustrated in block diagram form.

The illustration in the drawings is schematically.

One component of the kit according to the present invention is a marker dye containing a polymethine with the general formula I. The substituted derivatives of indole, heteroindole, pyridine, chinoline or acridine of the general formula I can be used as dyes for the optical marking or labelling of proteins, in particular of lipoproteins.

The labelling of proteins can be done by the formation of ionic or non-ionic interaction between the markers of general formula I and the proteins to be labelled. Alternatively, the functional groups of these markers activated with regards to nucleophiles can couple covalently with an OH, $NH_2$ or SH function, which therefore creates a system for the qualitative and quantitative determination of proteins, in particular of lipoproteins.

The coupling or conjugation reaction can take place in an aqueous or mostly aqueous solution and preferably at room temperature. During this reaction, a conjugate of a lipoprotein with the marker dye having fluorescent properties is created.

By labelling lipoproteins with the above-described non-symmetrical polymethines, which on the one hand have an easily derivatizable heterocycle of the type of the pyridine, chinoline, indole, heteroindole or acridine derivatives, and on the other hand have a 6-ring heterocycle, in particular the following advantages are achieved:

In contrast to fluorescent dyes, which fluoresce independently of a formation of a conjugate with the proteins to be detected and therefore have to be separated from the sample to be analysed before the detection step, the marker dyes according to the present invention have essentially no fluorescent properties in an un-conjugated state. Further, the marker dyes according to the present invention selectively associate with the unique micelle-like structure of lipoproteins characterized by hydrophobic residues in the interior and hydrophilic residues on the exterior of the lipoprotein aggregates. Due to fluorescent properties of such a conjugate between a lipoprotein and the marker dye containing a polymethine having the general formula I a selective labelling of lipoproteins can be achieved.

By using the kits of the present invention, not only lipoproteins can be selectively detected but also HDL and LDL sub-class patterns of lipoproteins may be analysed.

As is apparent for the person skilled in the art, this advantage not only holds true for lipoproteins, but for all kinds of micelle-like structures such as proteins which are solubilized in a sufficient amount of SDS (sodium dodecyl sulphate), so that micelles are formed.

Further, trimethines according to the general formula I already absorb in the spectral range greater than 650 nm and have a significantly improved photochemical and thermal stability when compared to other polymethines known in the prior art.

By means of molecular engineering, it is possible to control the position and intensity of the absorption and emission maxima at will and to adapt them to emission wavelengths of different excitation lasers, in particular near infrared (NIR) laser diodes.

The marker dyes can be produced by a relatively simple two-step synthesis with which a variety of dyes with functionalities that differ, for example, with regards to the total charge of the dye and the number, specificity and reactivity of the activated group used for the immobilization can be provided in a manner that is specific to the respective application. Polymethines having the general formula I are described in U.S. Pat. No. 6,750,346 which is incorporated herein by reference in its entirety.

Compounds with the general formula I as well as systems derived from them i.e. conjugates of proteins such as lipoproteins and the polymethines of the general formula I, can be used in optical, in particular fluorescence optical qualitative and quantitative determination methods for electrophoresis, chromatography and electrochromatography.

According to a preferred embodiment, the separation channel is adapted for separating different compounds electrophoretically, chromatographically or electrochromatographically. E.g., a chip for performing an electrophoretic separation comprises a base substrate comprising a main surface, wherein a channel is formed in said main surface of said base substrate in at least one direction.

According to a further preferred embodiment, the kit further comprises a separation gel. Examples of appropriate materials for inclusion in this gel comprise polyacrylamide, polydimethylacrylamide, polyethylene oxide and/or polyvinylpyrrolidone. A preferred gel is a polydimethylacrylamide (PDMA) gel.

Optionally, the medium may also comprise a denaturing agent such as N-methylurea.

The chip may further comprise an element for applying an electric field across the separation channel or the medium. The electric field is applied across said separation channel by turning on a voltage. On the basis of said separation mechanism a separation of the compounds in the samples is performed.

In particular, the kit according to the present invention can be employed in various electrophoretic techniques. Non-limiting examples of electrophoretic techniques include SDS polyacrylamide gel electrophoresis (SDS-PAGE), capillary electrophoresis, and micro-channel/microfluidic channel electrophoresis.

A preferred type of electrophoresis to employ the kit is microfluidic-channel electrophoresis.

Another component of the kit according to the present invention which may also be used in the methods according to the present invention is a chip for performing a separation of macromolecular species such as proteins and in particular lipoproteins.

If the kit is used for microfluidic-channel electrophoresis, it preferably involves a micro-channel chip having a network of micro-channels that serve as paths for the migration of fluid sample volumes. A single sample volume or many sample volumes may be run on the same micro-channel chip simultaneously. The micro-channel chip is loaded into a device, such as a bioanalyzer for molecular assays (e.g., an Agilent 2100 bioanalyzer), which provides a network of microelectrodes onto the chip wells, thus supplying the necessary voltages and currents for the separation of the sample volume components. Micro-channel chip electrophoresis generally provides higher resolutions, smaller sample volume sizes, shorter analysis times, and reduced sample handling over traditional capillary electrophoresis. An example of this type of electrophoresis is described in U.S. Pat. No. 6,042,710, which is hereby incorporated herein by reference in its entirety.

When used for microfluidic-channel electrophoresis, the chip can have electrodes and a substrate which comprises a planar body structure in which grooves are fabricated to define capillary channels when overlaid with a cover element, also typically planar in structure. Exemplary substrates materials include, e.g. glass, quartz, silica, silicon, polymers, e.g. plastics like polydimethylsiloxanes (PDMS), polymethylmethacrylate (PMMA), polyurethane, polyvinylchloride (PVC), polystyrene, polysulfone, polycarbonate, polytetrafluoroethylene (Teflon™), and a variety of others that are well known in the art. Substrates may take a variety of shapes or forms, including tubular substrates, e.g. polymer or fused silica capillaries, or the like. In preferred aspects, however, the substrate comprises a planar body structure in which grooves are fabricated to define capillary channels when overlaid with a cover element, also typically planar in structure. Examples of such planar capillary systems are described in U.S. Pat. No. 5,976,336 and are incorporated herein by reference in its entirety. The medium is employed in the micro-channels formed in the substrate to bring about the separation of sample components passing through the micro-channels under the influence of an electric field induced across the medium by the electrodes.

Capillary channels also can be of a variety of different shapes in cross-section, including tubular channels, rectangular channels, rhomboid channels, hemispherical channels or the like, or even more arbitrary shapes such as may result from less precise fabrication techniques, e.g. laser ablation. Typically, the shape of a capillary channel will vary, depending upon the substrate type used and the method of propagation. For example, in typical fused silica capillaries, the capillary channel will be tubular. In systems employing planar substrates, channels will typically comprise either a rhomboid, rectangular or hemispherical cross sectional shape, depending upon the substrate material and method of fabrication of the channels.

A variety of manufacturing techniques are well known in the art for producing microfabricated channel systems. For example, where such devices utilize substrates commonly found in the semiconductor industry, manufacturing methods regularly employed in those industries are readily applicable, e.g. photolithography, wet chemical etching, chemical vapour deposition, sputtering, electroforming, etc. Similarly, methods of fabricating such devices in polymeric substrates are also readily available including injection molding, embossing, laser ablation, LIGA techniques and the like. Other useful fabrication techniques include lamination or layering techniques, used to provide intermediate micro-scale structures to define elements of a particular micro-scale device.

Typically, the capillary channels will have an internal cross-sectional dimension, e.g. width, depth, or diameter, of between about 1 µm and about 500 µm, with most such channels having a cross-sectional dimension in the range of from about 10 µm to about 200 µm.

In particular, the preferred aspects, planar micro-fabricated devices employing multiple integrated micro-scale capillary channels are used. Briefly, these planar micro-scale devices employ an integrated channel network fabricated into the surface of a planar substrate. A second substrate is overlaid on the surface of the first to cover and seal the channels, and thereby define the capillary channels.

Preferably, the chip of the kit according to the present invention is provided with one or more analysis channels or separation channels or separation flow paths and comprises additional channels connecting the analysis channel to multiple different sample reservoirs. These reservoirs are generally defined by apertures disposed in the second overlaying substrate, and positioned such that they are in fluid communication with the channels of the device. A variety of specific channel geometries are employed to optimise channel layout in terms of material transport time, channel lengths and substrate use. Examples of such micro-scale channel network systems are described in detail in WO 98/49548, U.S. Pat. No. 6,235,175, U.S. Pat. No. 6,153,073, U.S. Pat. No. 6,068,752, U.S. Pat. No. 5,976,336 and U.S. application Ser. No. 60/060,902, which are all incorporated herein by reference in its entirety.

Introduction of the separation gel or medium into a capillary channel or micro-channel may be as simple as placing one end of the channel into contact with the medium and allowing the medium to wick into the channel. Alternatively, vacuum or pressure may be used to drive the medium solution into the capillary channel. In integrated channel systems such as those used in chip electrophoresis, the medium is typically placed into contact with a terminus of a common micro-channel, e.g. a reservoir disposed at the end of a separation channel, and slight pressure is applied to force the polymer into all of the integrated channels.

A preferred method according to the present invention, in particular if the separation is performed electrophoretically, comprises the following steps:
injecting the sample into a chip, wherein the chip comprises at least one well for receiving the sample, and a separation channel coupled to the at least one well and being adapted for separating different compounds; and
applying an electric field across the channel to move the sample through the channel.

A sample containing proteins or lipoproteins for which separation is desired is preferably placed in one end of the separation channel and a voltage gradient is applied along the length of the channel. As the sample components are electrokinetically transported down the length of the channel and through the medium disposed therein, those components are resolved. The separated components are then detected at a point along the length of the channel, typically near the terminus of the separation channel distal to the point at which the sample was introduced.

The separation in the method according to the present invention is preferably performed at a pH in the range of from about 7 to about 8, more preferably at a pH in the range of from about 7.3 to about 7.7 and most preferred at pH of about 7.5.

Further, it is preferred that the sample containing proteins or lipoproteins for which separation is desired comprises sodium dodecyl sulphate, preferably in an amount of from about 0.10 to about 0.20 mM, more preferably in an amount of from about 0.125 to about 0.175 mM and most preferred in an amount of about 0.15 mM.

The marker according to the general formula I dye may be injected into the chip together with the sample to be analyzed, or before or after the sample has been injected. Alternatively or in addition, the marker dye according to the general formula I may be contained in the separation gel. If the marker dye according to the general formula I is present in the separation gel it may serve to focus the detection device.

Detection of separated species is typically carried out using a fluorescent detection system that is well known in the art. Typically, such detection systems operate by detecting fluorescence of the marker dye which contains a polymethine of the general formula I as described above. Typically, such systems utilize a light source capable of directing light energy at the separation channel as the separated species are transported past. The light source typically produces light of an appropriate wavelength to activate the labelling group. Fluorescent light from the labelling group is then collected by appropriate optics, e.g. an objective lens, located above, below or adjacent the capillary channel, and the collected light is directed at a photometric detector, such as a photodiode or photomultiplier tube. The detector is typically coupled to a computer, which receives the data from the detector and records that data for subsequent storage and analysis.

Before a sample comprising a plurality of unknown species is analysed, the measurement set-up is usually calibrated. Hence, it is preferred, that the kit further comprises a calibration sample. The calibration sample can be selected from a large variety of different calibration samples comprising a set of well-known compounds of different size such as SRM 1951b—Lipids in Frozen Human, Serum, Level 1 (NIST, Gaithersburg, Md., USA), Ultra HDL calibrator vial, 1 ml (Genzyme Diagnostics, West Malling Kent, ME, UK), Human HDL, 10 mg; Human LDL, 5 mg; Human Ox. LDL, 2 mg; Human Lp(a), 0.1 mg (all available at BTI, Biomedical Technologies, Inc., MA, USA), AutoHDL/LDL Calibrator, 3 ml; HDL Standard, 15 ml (both available at Eco-Scientific, Rope Walk, Thrupp, Stroud, UK), Lipid Control Levels 1, 2 and 3 (all available at Polymedco, Inc., Cortland Manor, N.Y., USA), Low total cholesterol, TCh @ 50 mg/dL, LRC LEVEL 1; Normal total cholesterol, TCh @ 165-180 mg/dL, TG<100 mg/dL, LRC LEVEL 2; Elevated total cholesterol, TCh @ 265, TG @ 230; LRC LEVEL 3; High Density Lipoprotein, HDL @ 50, LRC LEVEL 4 (all available at Solomon Park Research Laboratories, Kirkland, Wash., USA), and HDL Reference Pools ID 204 (TV (SD) 60.1 (0.7) mg/dL), ID 205 (TV (SD) 30.5 (0.8) mg/dL), ID 301 (TV (SD) 49.5 (1.2) mg/dL), ID 303 (TV (SD) 50.6 (1.4) mg/dL), ID 305 (TV (SD) 30.8 (0.8) mg/dL), ID 307 (TV (SD) 40.5 (0.9) mg/dL) (all available at Centers for Disease Control and Prevention Atlanta, Ga. 3034, USA; note: pools may be prepared according to the Lipid Standardization Program (LSP)).

It is particularly preferred that a so-called ladder is used as a calibration sample. A ladder is a calibration sample comprising a plurality of well-known components, whereby the name "ladder" is due to the fact that the calibration peak pattern looks like a ladder of peaks related to the various components. Because the set of calibration peaks looks like a ladder, calibration samples are often referred to as "ladders". A lot of manufacturers in the field of DNA analysis and protein analysis produce calibration samples or "ladders" for electrophoresis systems, chromatography systems or electrochromatography systems. E.g., in protein analysis, calibration samples comprising a set of different proteins are used.

In case fluorescence detection is used for detecting different species, ladders comprising fragments labelled with fluorescence tags may be employed. When the species of the calibration sample are stimulated with incident light, the tags attached to the species emit fluorescence light. Calibration samples or "ladders" comprising a marker that fluoresces at a first wavelength, and a set of labelled fragments that emit fluorescent light at a second wavelength may also be employed.

After the fluorescent peak pattern of the calibration sample has been acquired, a sample of interest is analysed. In order to allow for an alignment with the calibration peak pattern, a certain concentration of the marker and a certain concentration of the largest labelled ladder fragment may be added to the sample of interest. Then, the compounds of the sample of interest are separated, and the samples bands obtained at the separation column's outlet are analysed.

According to another preferred embodiment, the marker dye according to formula I emits fluorescent light of a first wavelength, whereas the labelled fragments of the calibration sample emit fluorescence light of a second wavelength, which is different from the first wavelength. Some of the available ladders comprise two or more different fluorescence dyes adapted for emitting fluorescence light of two or more different wavelengths. Correspondingly, there exist fluorescence detection units adapted for simultaneously tracking fluorescence intensity at two or more wavelengths.

Preferred methods for peak pattern calibration are disclosed in European patent application 1 600 771 which is incorporated herein by reference in its entirety.

In the following, a preferred embodiment of the method of analysing proteins according to the present invention in described.

Initially, in the area of material flow, the materials to be examined, possibly in addition to the reagents required for the corresponding test such as the marker dyes having the general formula I, are fed to the microchip. Thereafter, these materials on the microchip are moved or transported, e.g. by means of electrical forces, pressure sources, thermal sources or the like. The feed and/or the movement of materials may be brought about by means of a suitable electronic control.

In this example, the materials are subjected to preliminary treatment before they undergo the test as such. This preliminary treatment may, for example, consist of preheating by means of a heating system or pre-cooling by means of a suitable cooling system, in order, for example, to fulfil the required thermal test conditions. As is known, the temperature conditions for execution of a chemical test usually exert a considerable influence on the cycle of test kinetics. Such a preliminary treatment can also take place in a multiple sequence, in which context a pre-treatment cycle and a further transport cycle are obviated. The above-mentioned pre-treatment can in this instance, in particular, fulfil the function of separation of materials such as to access only certain specified components of the initial materials for the corresponding test. Essentially, both the material quantity (quantity) and the material speed (quality) can be determined by means of the transportation as described. In particular, precise adjustment of material quantity enables precise metering of individual materials and material components. Further, the latter processes can advantageously be controlled by means of electronic control.

After one or more optional pre-treatments, the actual experimental test/examination takes place, in which context the test results can be detected on a suitable detection point of the chip or microchip. Detection advantageously takes place by means of optical detection, e.g. by a laser diode in conjunction with a photoelectric cell, or a mass spectrometer, which may be connected or by means of electrical detection. The resultant optical measurement signals are then fed to a signal-processing system and thereafter to an analysis unit (e.g. a suitable microprocessor) for interpretation of the measurement results.

The operational components typically used for a chip contained in the kit according to present invention described herein are schematically illustrated in FIG. 1. These are mainly subdivided into the components relating to a material transport or flow 1, and those which represent the information flow 2 arising upon execution of a test. Material flow 1 typically includes sampling operations 3 and operations for transporting 4 materials on the chip, as well as optional operations for treatment or pre-treatment 5 of the materials to be examined. Furthermore, a sensor system 6 is typically employed to detect the results of a test and, optionally, to monitor the material flow operations, so that adjustments can be made in controlling material flow using the control system. One example of the control mechanism is shown as control electronics 7. Data obtained in the detection operation 6 and 6' is transferred typically to the signal processing 8 operation so that the detected measurement results can be analysed. A priority objective in the design of such microchip systems is the provision of function units/modules corresponding to the above-mentioned functions and the establishment of suitable interfaces between individual modules. By means of a suitable definition of these interfaces, it is possible to achieve a high degree of flexibility in adapting the systems to various microchips or experimental arrangements. Furthermore, on the basis of such a strictly modular system structure, it is possible to achieve the most extensive level of compatibility between various microchips and/or microchip systems.

Initially, in the area of material flow, the materials to be examined (possibly in addition to the reagents required for the corresponding test) are fed to the microchip 3. Thereafter, these materials on the microchip are moved or transported, e.g., by means of electrical forces 4. Both the feed and the movement of materials are brought about by means of a suitable electronic control 7, as indicated by means of the dotted line. In this example, the materials are subjected to preliminary treatment 5, before they undergo the test as such. This preliminary treatment may, for example, consist of pre-heating by means of a heating system or pre-cooling by means of a suitable cooling system in order, for example, to fulfill the required thermal test conditions. As is known, the temperature conditions for execution of a chemical test usually exert a considerable influence on the cycle of test kinetics. As is indicated by the arrow, this preliminary treatment can also take place in a multiple sequence, in which context there are obviated a pretreatment cycle 5 and a further transport cycle 4'. The above-mentioned pretreatment can in this instance, in particular, fulfill the function of separation of materials such as to access only certain specified components of the initial materials for the corresponding test. Essentially, both the material quantity (quantity) and the material speed (quality) can be determined by means of the transportation as described. In particular, precise adjustment of material quantity enables precise metering of individual materials and material components. Furthermore, the latter processes can advantageously be controlled by means of electronic control 7.

After one or more pre-treatments, the actual experimental test/examination takes place, in which context the test results can be detected on a suitable detection point of the microchip 6. Detection advantageously takes place by means of optical detection, e.g. a laser diode in conjunction with a photoelectric cell, a mass spectrometer, which may be connected, or by means of electrical detection. The resultant optical measurement signals are then fed to a signal-processing system 8, and thereafter to an analysis unit (e.g. suitable microprocessor) for interpretation 9 of the measurement results.

Following the above-mentioned detection 6, there is the option of implementation, as indicated by the dotted line, of further test series or analyses or separation of materials, e.g., those in connection with various test stages of a chemical test cycle which is, overall, more complicated. For this purpose, materials are transported onwards on the microchip after the first detection point 6, and to a further detection point 6'. There, the procedure theoretically defined according to stages 4' and 6 is performed. Finally, the materials are fed, after termination of all reactions/tests, to a material drain (not illustrated here) by means of a concluding transport cycle or collection cycle 4'''.

Further incentives for miniaturizations in the field of chemical analysis include the ability and desirability to minimize the distance and time over which materials are transported. In particular, the amount of time and distance required to transport materials between the sampling of the materials and the respective detection point of any chemical reaction that has taken place shall be minimized. It is furthermore known from the field of liquid chromatography and electrophoresis that separation of materials can be achieved more rapidly and individual components can be separated with a higher degree of resolution than has been possible in conventional systems. Furthermore, micro-miniaturized laboratory systems enable a considerably reduced consumption of materials, particularly reagents, and a far more efficient intermixing of the components of materials. A preferred apparatus for the operation of a microfluidic device, i.e. a microchip laboratory system for chemical processing or analysis, is described in WO 00/78454 which is incorporated herein by reference in its entirety.

Figure 2:
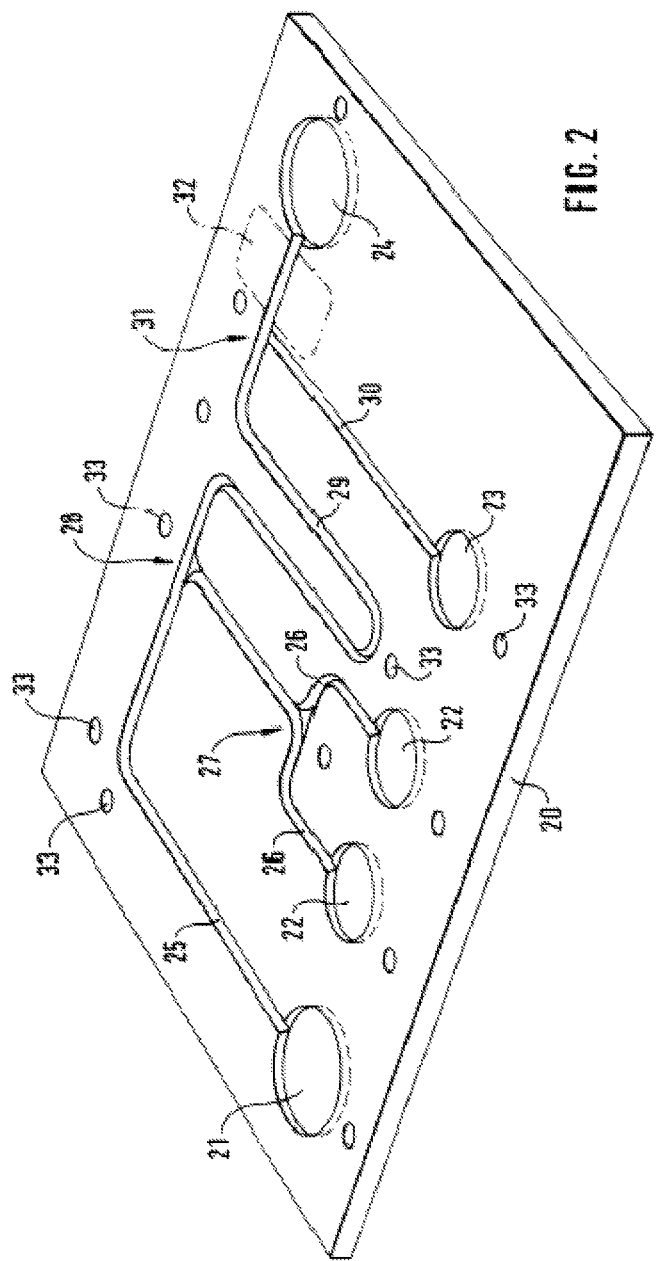
FIG. 2 schematically illustrates an exemplary chip for utilization in a kit according to the present invention.

FIG. 2 shows an exemplary laboratory microchip or chip which is suitable for utilization in a kit or method according to the invention. On the upper side of a substrate 20, microfluidic structures are provided, through which materials are transported. Substrate 20 may, for example, be made up of glass or silicon, in which context the structures may be produced by means of a chemical etching process or a laser etching process. Alternatively, such substrates may include polymeric materials and be fabricated using known processes such as injection molding, embossing and laser ablation techniques. Typically, such substrates are overlaid with additional substrates in order to seal the conduits as enclosed channels or conduits.

For sampling of the material to be examined (hereinafter called the "sample material") onto the microchip, one or several recesses 21 are provided on the microchip, to function as reservoirs for the sample material. In performing a particular exemplary analysis or test, the sample material is initially transported along a transport duct or channel 25 on the microchip. In this example, transport channel 25 is illustrated as a V-shaped groove for convenience of illustration. However, the microfluidic substrates typically comprise sealed rectangular (or substantially rectangular) or circular-section conduits or channels.

The reagents required for the test cycle are typically accommodated in recesses 22 which also fulfil the function of reagent and/or sample material reservoirs. In this example, two different materials could readily be manipulated. By means of corresponding transport conduits 26, these are initially fed to a junction point 27, where they intermix and, after any chemical analysis or synthesis has been completed, constitute the product ready to use. At a further junction 28 this reagent meets the material sample to be examined, in which the two materials will also intermix.

The material formed then passes through a conduit section 29 which may have a meandering geometry which functions to achieve artificial extension of the distance available for reaction between the material specimen and the reagent. In a further recess 23 configured as a material reservoir, in this example, there is contained a further reagent which is fed to the already available material mix at a further junction point 31.

The reaction of interest takes place after the above-mentioned junction point 31, which reaction can then be detected, ideally by contactless means, e.g. optically, within an area 32 (or measurement zone) of the transport duct by means of a detector. In this context, the corresponding detector can be located above or below area 32. After the material has passed through the above-mentioned area 32, it is fed to a further recess 24 which represents a waste reservoir or material drain for the waste materials which have been produced, overall, in the course of the reaction.

Finally, on the microchip there are provided recesses 33 which act as contactless surfaces for application of electrodes and which in turn enable the electrical voltages, and even high voltages, required for connection to the microchip for operation of the chip. Alternatively, the contacting for the chips can also take place by means of insertion of a corresponding electrode point directly into the recesses 21, 22, 23 and 24 provided as material reservoirs. By means of a suitable arrangement of electrodes 33 along transport conduits 25, 26, 29 and 30 and a corresponding chronological or intensity-related harmonization of the applied fields, it is then possible to achieve a situation in which the transportation of individual materials takes place according to a precisely dictated time/quantity profile, such that it is possible to achieve very precise consideration of and adherence to the kinetics for the underlying reaction process.

In pressure-driven transport of materials within the microfluidic structure, it is typically necessary to make recesses 33 such that corresponding pressure supply conduits closely and sealably engage them so as to make it possible to introduce a pressurized medium, for example in inert gas, into the transport conduits, or apply an appropriate negative pressure.

Figure 3:
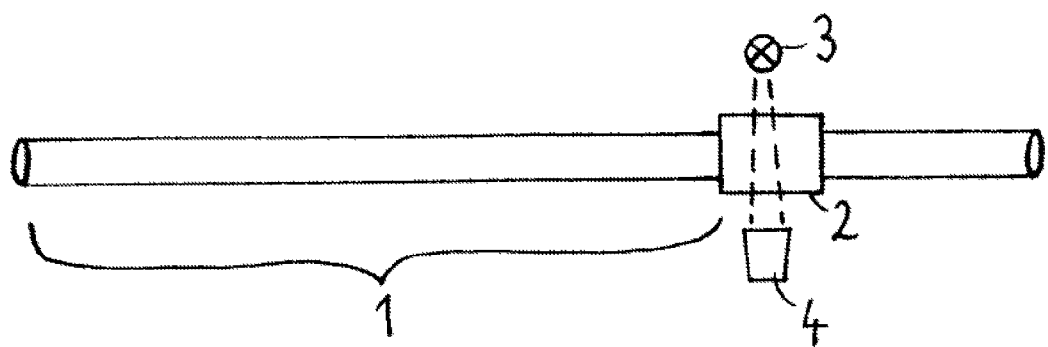
FIG. 3 schematically illustrates a further exemplary chip for utilization in a kit according to the present invention.

FIG. 3 shows a further exemplary measurement set-up for separating and analysing a fluid sample comprising a plurality of different sample compounds. Each of the sample compounds is characterized by an individual migration time required for travelling through a separation flow path 1. The separation flow path 1 might e.g. be an electrophoresis flow path, a chromatography flow path or an electric chromatography flow path. At the outlet of the separation flow path, a detection cell is located. The detection cell might e.g. be implemented as a fluorescence detection cell 2 comprising a light source 3 and a fluorescence detection unit 4. The fluorescence detection cell 2 is adapted for detecting sample bands of fluorescence-labelled species as a function of time.

Figure 4:
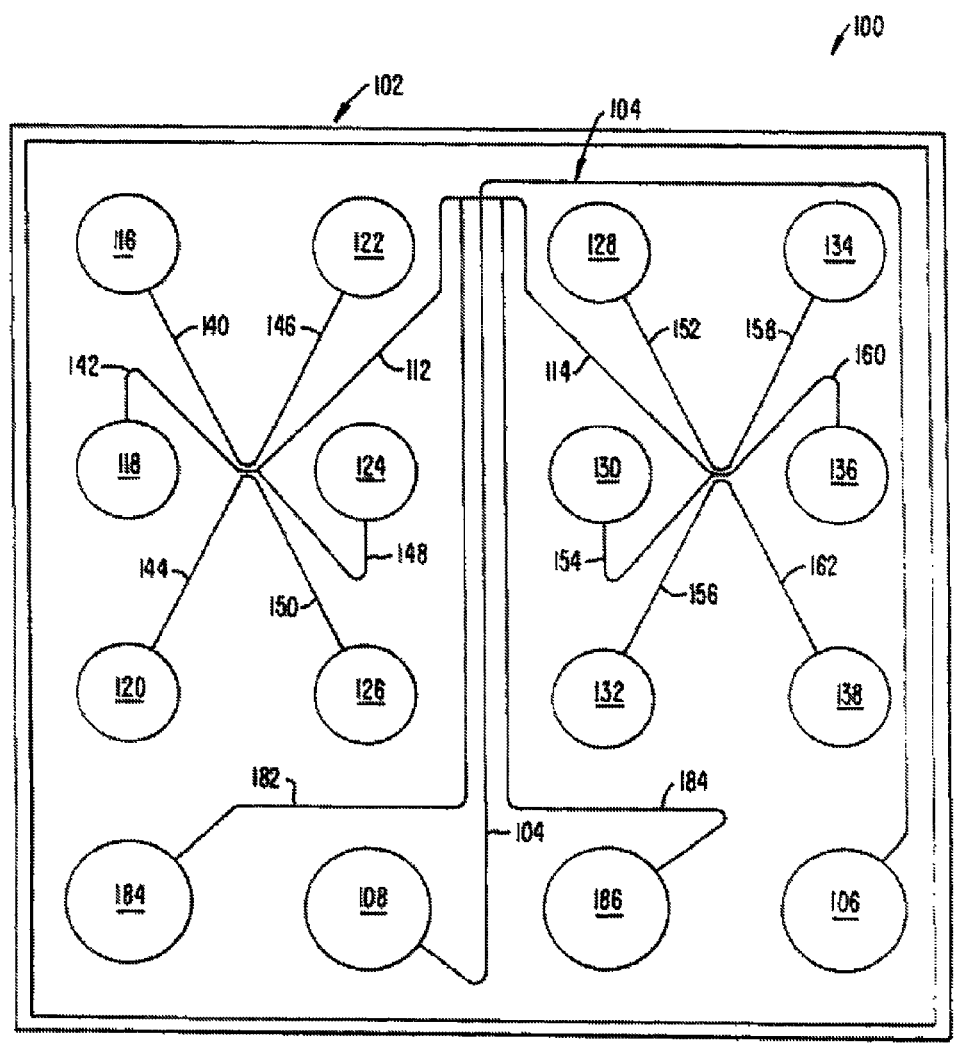
FIG. 4 schematically illustrates another exemplary microscale electrophoresis device or chip for use in electrophoretic separation of proteins such as lipoproteins for use in the present invention

FIG. 4 shows a further specific example of channel geometry of a chip in a kit according to the present invention. In operation, sample materials are placed into one or more of the sample reservoirs 116-138. A first sample material, e.g., disposed in reservoir 116, is then loaded by electrokinetically transporting it through channels 140 and 112, and across the intersection with the separation channel 104, toward load/waste reservoir 186 through channel 184. Sample is then injected by directing electrokinetic flow from buffer reservoir 106 through analysis channel 104 to waste reservoir 108, while pulling back the sample in the loading channels 112: 114 at the intersection. While the first sample is being separated in analysis channel 104, a second sample, e.g., that disposed in reservoir 118, is preloaded by electrokinetically transporting it into channels 142 and 112 and toward the load waste reservoir 184 through channel 182. After separation of the first sample, the second sample is then loaded across the intersection with analysis channel 104 by transporting the material towards load/waste reservoir 186 through channel 184.

Further methods of electrophoretically separating macromolecular species such as proteins, as well as compositions, systems, devices or chips useful in carrying out such methods are described in U.S. Pat. No. 6,042,710 which is incorporated herein by reference in its entirety.

Other preferred devices for operating a microchip with a microfluid structure for chemical, physical and/or biological processing are described in European patent application 1 360 992 and international patent application WO 00/78454 which are both also incorporated herein by reference in its entirety.

All publications and patent applications are herein incorporated by reference to the same extent as if each individual publication or patent application was specifically and individually indicated to be incorporated by reference in its entirety. Although the present invention has been described in some detail by way of illustration and example for purposes of clarity and understanding, it will be apparent that certain changes and modifications may be practised within the scope of the dependent claims.

It should be noted that the term "comprising" does not exclude other elements or features and the "a" or "an" does not exclude a plurality. Also elements described in association with different embodiments may be combined. It should also be noted that reference signs in the claims shall not be construed as limiting the scope of the claims.

The invention is subsequently to be illustrated in more detail by means of an embodiment example.

EXAMPLE

In the following a typical application of the kit according to the present invention for the separation of lipoproteins is shown:

The sample buffer contains the following reagents
200 mM TAPS(N-Tris(hydroxymethyl)methyl-3-aminopropanesulfonic acid), pH 7.5 (Sigma, Deisenhofen, Germany)
6 μM dye V02-04064 (Dyomics, Jena, Deutschland) as the staining marker dye
1 μM Alexa 700 (Invitrogen—Molecular Probes, USA) as the lower marker for calibration
1 μM dye 676 (Dyomics) as the upper marker for calibration
0.15 mM SDS (sodium dodecyl sulfate) (Sigma)

Figure 5:
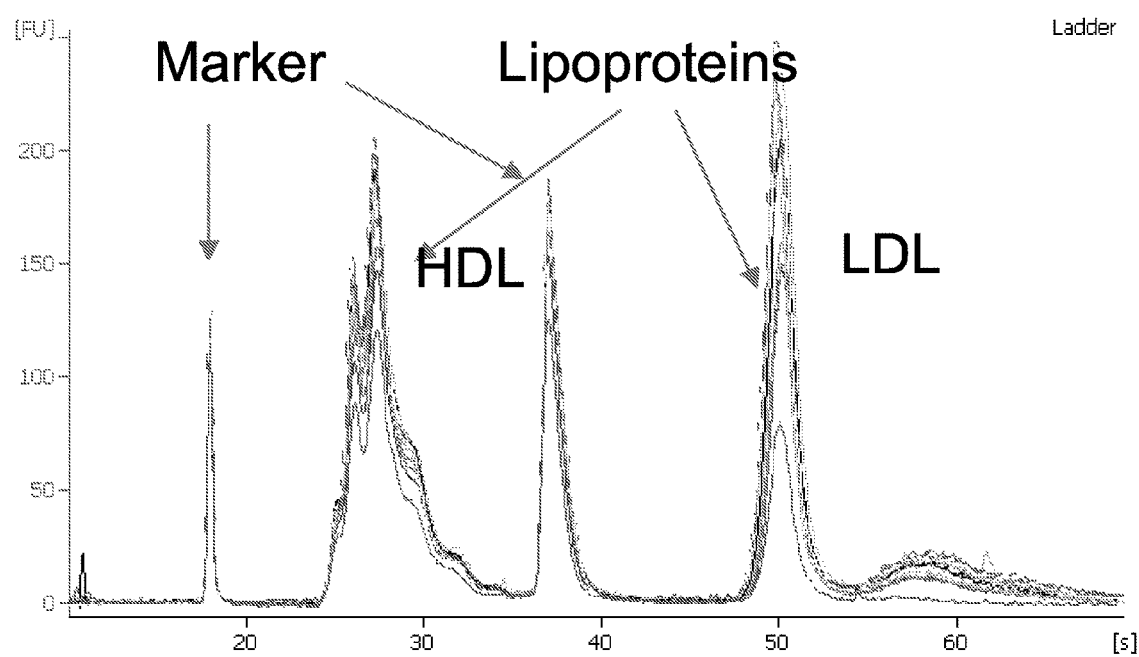
FIG. 5 shows an electropherogram of a serum sample analyzed on a microfluidic chip with the bioanalyzer according to example 1 (overlay of several electropherograms of the same sample run over an entire chip).
Figure 6:
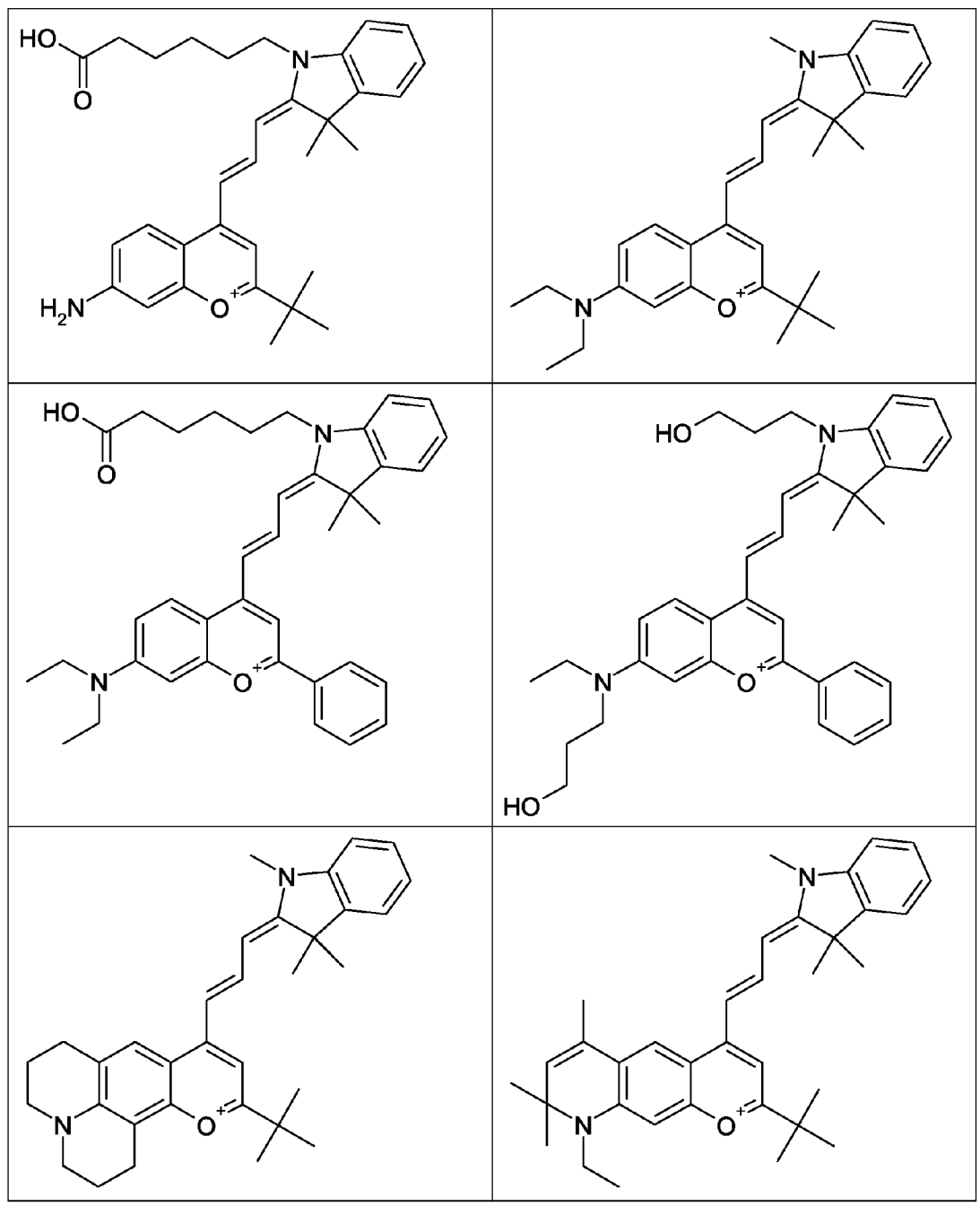
FIG. 6 shows the chemical formulae of exemplary marker dyes which are suitable for use in a kit according to the present invention.
Figure 7:
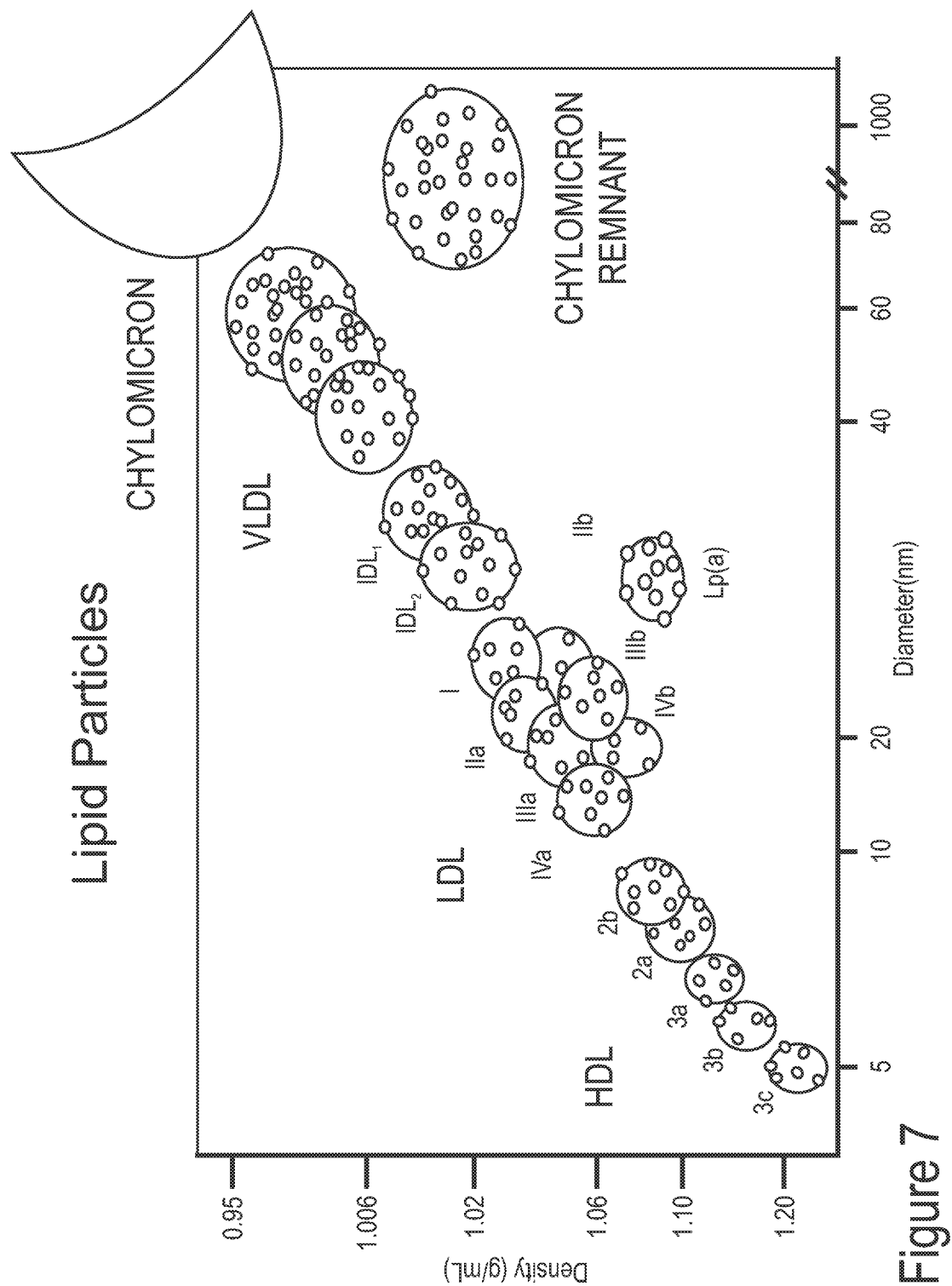
FIG. 7 shows a correlation between diameter and density of lipid particles.
Figure 8:
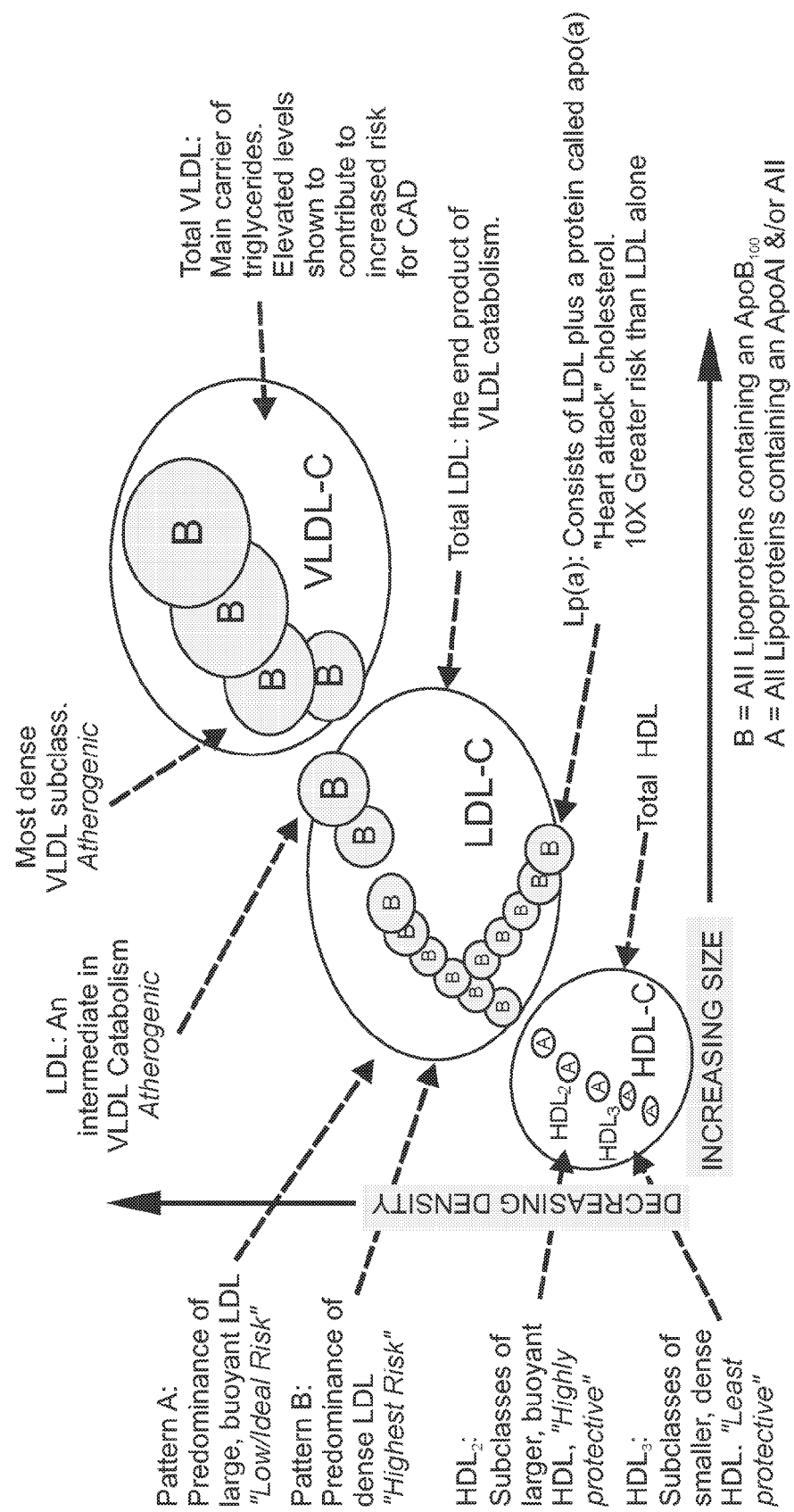
FIG. 8 shows the correlation of different lipoproteins with cardiac risk.

The separation gel or gel matrix contains the following reagents:
2% PDMA 12164 (Polysciences; USA; lot No.: 537426)
200 mM TAPS(N-Tris(hydroxymethyl)methyl-3-aminopropanesulfonic acid), pH 7.5 (Sigma)
0.15 mM SDS (Sigma)
0.15 μM dye V02-04064 (Dyomics) as the dye for focusing the detector The following assay protocol was used:
Take 1 µL of 12 different human serum samples and mix with 49 µL each of sample buffer containing dye.
Take 1 µL of serum standard and mix with 49 µl each of sample buffer containing dye.
Place chip on primer station.
Label each chip.
Add 10 µL of 2% gel matrix to the gel well.
Pressurize the well for 1 min.
Fill the other two gel wells with 10 µL gel matrix.
Add 10 µl of diluted serum standard in sample buffer to the standard well
Add 7 µL of each diluted sample in sample buffer to each of the 12 sample wells.
Place chip into instrument and start run.
For performing the assay, the Agilent 2100 Bioanalyzer (Agilent Technologies, USA) was used.
A typical electropherogram of a serum sample analyzed on a microfluidic chip with the bioanalyzer is shown in FIG. 5.

The invention claimed is:

1. A method of analyzing lipoproteins in a sample, the method comprising:
  labeling the lipoproteins in a sample with a marker dye containing a polymethine of the general formula I

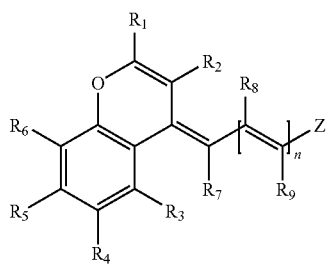

wherein Z has the general formula IIa

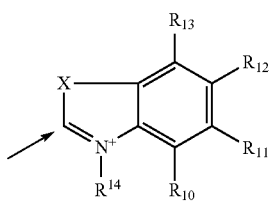

and wherein
X is $C(CH_3)_2$,
n is 1,
$R_1$ is —$C(CH_3)_3$;
$R_2$, $R_3$, $R_4$, $R_6$, $R_7$, $R_8$, $R_9$, $R_{10}$, $R_{11}$, $R_{12}$ and/or $R_{13}$ is hydrogen;
$R_5$ is —$N(CH_2CH_3)_2$;
$R_{14}$ is —$(CH_2)_3$—OH, —$(CH_2)_5$—COOH, or —$CH_3$;
performing on a microfluidic device a separation of the labeled lipoproteins in the sample; and
optically detecting the separated labeled lipoproteins.

2. The method of claim 1, wherein the separation is performed electrophoretically, chromatographically or electrochromatograpically.

3. The method of claim 2, wherein the electrophoretic separation is selected from the group consisting of SDS polyacrylamide electrophoresis (SDS-PAGE), capillary electrophoresis and microchannel/microfluidic channel electrophoresis.

4. The method of claim 2, wherein the microfluidic device comprises at least one reservoir for receiving the sample coupled to a separation channel adapted for separating different compounds, wherein performing the electrophoretic separation comprises:
  injecting the sample into the at least one reservoir; and
  applying an electric field across the channel to move the sample through the channel.

5. The method of claim 1, wherein the separation is performed on a separation gel selected from the group consisting of polyacrylamide, polydimethylacrylamide, polyethylene oxide, and polyvinyl pyrrolidone.

6. The method of claim 4, wherein the microfluidic device comprises a material selected from the group consisting of glass, quartz, silica, silicon, and polymers.

7. The method of claim 1, wherein the separation is performed at a pH in the range of from about 7 to about 8.

8. The method of claim 1, wherein the sample comprises sodium dodecyl sulphate in an amount of from about 0.10 to about 0.20 mM.

9. The method of claim 1, wherein a calibration is performed before analysis.

10. The method according to claim 9, wherein the calibration is performed with a "ladder".

11. The method of claim 1, wherein the separated and labeled lipoproteins are optically detected by fluorescence spectroscopy.

12. A method of optically detecting lipoproteins in a sample, wherein the method comprises:
  labeling the lipoproteins in a sample with a marker dye containing a polymethine of the general formula I

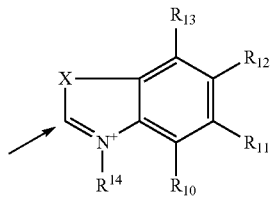

wherein Z has the general formula IIa and wherein
X is $C(CH_3)_2$,
n is 1,
$R_1$ is —$C(CH_3)_3$;
$R_2$, $R_3$, $R_4$, $R_6$, $R_7$, $R_8$, $R_9$, $R_{10}$, $R_{11}$, $R_{12}$ and/or $R_{13}$ is hydrogen;

$R_5$ is —N(CH$_2$CH$_3$)$_2$; and
$R_{14}$ is —(CH$_2$)$_3$—OH, —(CH$_2$)$_5$—COOH, or —CH$_3$; and
performing a separation of the labeled lipoproteins in the sample; and
optically detecting the separated labeled lipoproteins.

13. The method of claim 1, wherein the polymethine is a compound having the following structure:

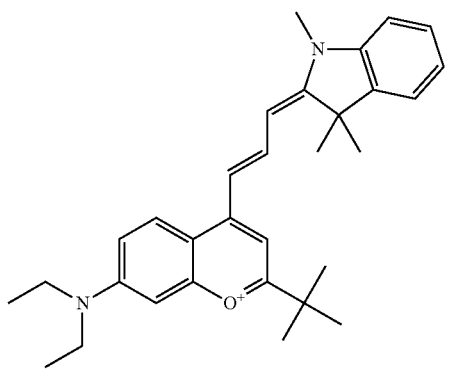

14. The method of claim 12, wherein the polymethine is a compound having the following structure:

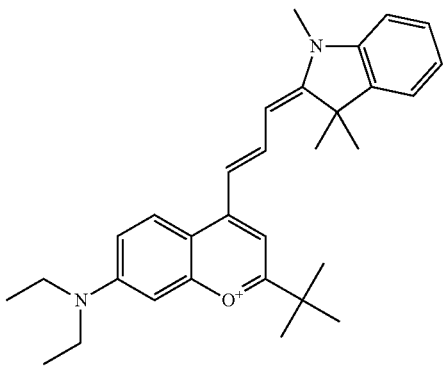

15. The method of claim 1, wherein un-conjugated marker dye is not separated from the labeled lipoproteins prior to the optically detecting step.

16. The method of claim 12, wherein un-conjugated marker dye is not separated from the labeled lipoproteins prior to the optically detecting step.

* * * * *